United States Patent [19]

Kim et al.

[11] Patent Number: 4,508,825

[45] Date of Patent: Apr. 2, 1985

[54] METHOD FOR THE SEPARATION OF EXTRACELLULAR AMYLASE AND PROTEASE PRODUCED DURING THE FERMENTATION OF ENZYME PRODUCING MICROORGANISMS

[75] Inventors: Chong Y. Kim; Terry F. Farver; Jack W. Brewer, all of Elkhart, Ind.

[73] Assignee: Miles Laboratories, Inc., Elkhart, Ind.

[21] Appl. No.: 480,245

[22] Filed: Mar. 30, 1983

[51] Int. Cl.³ .................... C12N 9/26; C12N 9/50; C12R 1/07
[52] U.S. Cl. .................................. 435/201; 435/219; 435/814; 435/816; 435/832
[58] Field of Search ................... 435/201–203, 435/219–225, 814, 816

[56] References Cited

U.S. PATENT DOCUMENTS 4,144,130  3/1979  Kula et al. .................... 435/210 X

OTHER PUBLICATIONS

Hustedt et al., *Biotechnology and Bioengineering*, vol. XX, pp. 1989–2005, (1978).
Albertsson, *Biochemistry*, vol. 12, No. 13, (1973), pp. 2525–2530.

*Primary Examiner*—Lionel M. Shapiro
*Attorney, Agent, or Firm*—Jerome L. Jeffers

[57] ABSTRACT

Extracellular protease and amylase coproduced during the fermentation of a microorganism capable of producing them are separated by the addition of polyethyleneglycol and a cationic epihalohydrin/polyamine copolymer or dextran polymer to the fermentation medium and allowing the polymers to phase separate to form a protease rich phase and an amylase rich phase.

12 Claims, No Drawings

METHOD FOR THE SEPARATION OF EXTRACELLULAR AMYLASE AND PROTEASE PRODUCED DURING THE FERMENTATION OF ENZYME PRODUCING MICROORGANISMS

BACKGROUND OF THE INVENTION

The production of industrial enzymes by the fermentation of microorganisms, whether they be fungi or bacteria, in an aqueous nutrient media is well-known. Depending on the nature of the particular microorganism, the enzyme(s) produced may be intracellular or extracellular. Various microorganisms produce two or more useful enzymes during fermentation. When one of the enzymes is intracellular and one is extracellular, enzyme separation is accomplished by separating the enzyme containing cells from the fermentation broth and recovering the intracellular enzyme. The extracellular enzyme can be recovered from the broth by conventional methods. An example of this type of separation is illustrated by co-pending application Ser. No. 425,713 where there is described the fermentation of an organism of the species *F. arborescens* to produce intracellular glucose isomerase and extracellular protease and separation of the enzymes by centrifugation of the glucose isomerase containing cells with recovery of the protease containing supernatant.

In some instances, such as where the enzyme must be solubilized by use of a detergent or by rupturing the cell walls, the separation of the solubilized enzyme from the cells or cell fragments can be problematical. This type of separation difficulty is described in U.S. Pat. No. 4,144,130 where it is pointed out that when the pullulanase produced by *Klebsiella pneumosiae* is removed from intact cells with detergents, separation of the cells from the supernatant by centrifugation requires uneconomically high g-numbers and separation by centrifugation is difficult because of the presence of the detergent. This patent discloses a method of separating the enzyme from the cells or cell fragments which involves feeding the fermentation broth into an aqueous solution of a low molecular weight, substituted or unsubstituted polyalcohol, polyether, polyester, polyvinylpyrrolidone or polysaccharide and an inorganic salt or a solution containing two of the high molecular weight compounds and separating the phases from each other which results in the cells or cell fragments being retained in one phase and the enzyme in the other. These patentees who also describe their work in *Biotechnology and Bioengineering*, Vol. XX, pages 1989-2005 (1978) wherein they disclose the use of dextran as a species of polysaccharide useful in this process.

A method for recovering phospholipase A from *Escherichia coli* in which the cells are homogenized, the cell liquid is separated by centrifugation and the enzyme is dissolved from the cell membrane all in a phase-distribution multi-phase system containing such immiscible polymers as polyethyleneglycol and dextran is disclosed in *Biochemistry*, Vol. 12, No. 13, 1973.

In certain fermentations, two useful, extra-cellular enzymes are produced, and since both enzymes are freely dispersed in the fermentation broth even after removal of the cells, their separation is difficult. An example of such a system is the fermentation in an aqueous nutrient medium of *Bacillus amyloliquefacieus* in which extracellular protease and amylase are produced. These enzymes are difficult to separate and it is an object of the present invention to provide a novel method for their separation.

SUMMARY OF THE INVENTION

The present invention is a method for the separation of extracellular protease and amylase produced during the fermentation in an aqueous nutrient medium of a microorganism capable of producing these enzymes. After conducting the fermentation and filtering the fermentation broth to provide a cell-free filtrate containing protease and amylase, these enzymes are separated by the steps of:

(a) adding a low molecular weight polyethyleneglycol and a high molecular weight polymer selected from the group of epihalohydrin/polyamine copolymers and dextran or a mixture thereof to the filtrate;

(b) providing sufficient agitation to mix the two polymers and the filtrate and allowing phase separation to occur between the polyethyleneglycol containing phase and the epihalohydrin/polyamine copolymer or dextran containing phase to thereby provide a polyethyleneglycol containing phase rich in protease relative to amylase and an epihalohydrin/polyamine copolymer or dextran containing phase rich in amylase relative to protease;

(c) separating the phases formed in step (b);

(d) recovering the enzymes in the polyethyleneglycol containing phase to provide a protease/amylase product rich in protease; and/or (e) recovering the enzymes in the epihalohydrin/polyamine copolymer or dextran containing phase to provide a protease/amylase product which is rich in amylase relative to protease.

DESCRIPTION OF THE INVENTION

The present enzyme separation method is predicated on the discovery that in a fermentation broth consisting of a nutrient medium in which a fermentation of an enzyme producing microorganism has been carried out to produce extracellular protease and amylase, the introduction of a relatively low molecular weight polyethyleneglycol and a relatively high molecular weight cationic epihalohydrin/polyamine copolymer or dextran with subsequent agitation of the medium results in phase separation of the polymers with the polyethyleneglycol phase being rich in protease and the epihalohydrin/polyamine copolymer or dextran phase being rich in amylase. Separation of the phases, precipitation of either the polymer or enzyme and removal of the precipitate by liquid/solid separatory techniques provides the purified enzyme.

Amylase and protease produced by either fungal or bacterial fermentation can be separated by this method. Thus, the chemical and physical properties of the fermentation broth of *Aspergillus orizae* would be sufficiently similar to that resulting from the fermentation of *Bacillus amyloliquefacieus* to permit separation of the coproduced amylase and protease by this method.

The high molecular weight cationic epihalohydrin/polyamine copolymer should have a molecular weight of from about 4,000 to 600,000 and preferably from about 15,000 to 25,000 to ensure good phase separation. Likewise, the low molecular weight polyethyleneglycol should have a molecular weight in the range of from about 1,000 to 10,000 and preferably from about 4,000 to 8,000.

Suitable epihalohydrin/polyamine copolymers can be prepared by the polymerization of an epihalohydrin and an alkylene polyamine. The degree of the polymerization determines the molecular weight of these polymers and suitable commercially polymers include BETZ-1180 (M.W. 15,000 to 50,000), BETZ-1185 (M.W. 10,000 to 20,000), BETZ-1190 (M.W. 8,000 to 14,000), and BETZ-1195 (M.W. 400,000 to 600,000). A preferred copolymer is commercially available under the trademark BETZ-1180 from Betz Laboratories, Inc., Trevose, PA. BETZ-1180 contains about 0.288 millimoles of amino groups per gram of solution (based on ninhydrin assay) and is marketed as a solution containing 30 weight percent solids, based on total solution weight. This polymer is described in U.S. Pat. Nos. 3,915,904 and 3,953,330. The polymer is described therein as a water-soluble cationic polymer obtained by the polymerization of an epihalohydrin with an alkylene polyamine having the formula $R_1R_2NRNH_2$ wherein R is a lower alkylene having from 2 to about 6 carbon atoms, and $R_1$ and $R_2$ are each a lower alkyl of from about 1 to about 6 carbon atoms, the mole ratio of epihalohydrin to polyamine being from about 0.60:1 to about 2.7:1, said polymerization comprising reacting with the alkylene polyamine from about 50 to about 90 percent of the amount of epihalohydrin to be polymerized, allowing the reaction to continue until the reaction medium attains a substantially uniform viscosity, and reacting the remaining portion of the epihalohydrin incrementally to obtain the cationic polymer, the temperature of polymerization being from 60° C. to about 120° C.

Dextran polymers suitable for use in the present invention have a molecular weight of from about 110,000 to 2,000,000 and preferably from about 400,000 to 600,000 and consist of linear chains of α-1-3 linkages. Substituted dextrans, dextran sulphate (such as the polyanionic derivative of dextran with an average molecular weight of 500,000) and DEAE-dextran (such as the diethylaminoethyl ether polycationic derivative having a average molecular weight of 500,000) have been tried in the method which is the subject matter of this invention. While some separation can be achieved with DEAE-dextran, the polyanionic dextran sulphate was found to be unsuitable.

In carrying out the invention, a microorganism capable of producing extracellular protease and amylase is allowed to grow in a suitable nutrient medium. After the fermentation sufficient polymer is added to cause the desired enzyme purification upon separation of the polymer phases. In the case of an epihalohydrin/polyamine copolymer, an amount of from 1.5 to 60 weight percent and in the case of dextran, an amount of from 0.5 to 15 weight percent of the aqueous nutrient medium is typically added. The low molecular weight polyethylene glycol is normally added in an amount of from 0.5 to 30 weight percent in the case where the epihalohydrin/polyamine copolymer is used and in an amount of from 1.0 to 10 weight percent of the filtrate when dextran is used. After agitation sufficient to cause close contact between the enzymes and polymers, the medium is allowed to stand until phase separation occurs and the enzyme is recovered as previously described.

The method of practicing the present invention is further illustrated by the following examples.

EXAMPLE I

A nutrient medium suitable for fermentation was prepared by adding the following ingredients to a 6,000 gallon fermentor:

| 1. Corn Steep Liquor | 1400 lbs. |
|---|---|
| 2. Soya Meal | 1600 lbs. |
| 3. Fish Meal | 550 lbs. |
| 4. Calcium Carbonate | 530 lbs. |
| 5. Mazu DF 6000* | 5 gals. |
| 6. Di Ammonium Phosphate | 130 lbs. |
| 7. Lactose | 4550 lbs. |
| 8. Water | 5800 gals. |

*an organic defoamer whose major ingredient is polypropyleneglycol.

The medium was inoculated with viable cells of *Bacillus Amyloliquefacieus* and allowed to ferment for 58-60 hours at 34° C. After this fermentation, the medium was filtered to provide 6,000 gallons of a cell-free filtrate containing both protease as determined by a Spectrophotometric Detergent Protease Assay which is a modification of the Delft Assay method developed by the Royal Netherlands Fermentation Industries, Ltd., Delft, Holland and amylase as determined by the Manual Liquefying Alpha-Amylase Assay which is a modification of the method disclosed by Wohlgemuth in *Biochem.*, Z9:1 (1908).

To the filtrate was added 1,674 gallons of Betz-1180 polymer and 11,544 pounds of polyethyleneglycol 8000 (PEG 8000 having an average molecular weight of 8,000) to provide a resultant made up of 65% (w/w) filtrate, 20% (w/w) of Betz-1180 and 15% (w/w) polyethyleneglycol 8000. This mixture was agitated vigorously with a motor driven stirrer until all the polyethyleneglycol was in solution. Upon storage at room temperature with some centrifugation, the mixture phase separated to form a top and bottom phase having a v/v ratio top to bottom of 3.27:1. The top phase was removed from the bottom phase by siphon.

The enzyme content of the top phase (PEG 8000) was determined to be 72.1% of the protease and 3.4% of the amylase originally present in the filtrate as determined by the assays previously mentioned. The bottom phase (Betz-1180) was found to contain 96.6% of the amylase and 27.9% of the protease.

To separate the amylase from the bottom (Betz-1180) phase there was added thereto tannic acid 40% (w/w) based on this phase and the resultant was mixed with a stirrer. A Betz-1180 tannic acid complex precipitated with the amylase remaining in solution. After removal of the precipitate by solid liquid separatory means, 84% of the original amylase was recovered by decantation.

Ethanol was added to the top (PEG) phase in a ratio of 2:1 to precipitate the protease. After separation, it was found that the precipitate contained 72% of the overall protease activity.

EXAMPLE II

A filtrate from the fermentation of *B. amyloliquefacieus* was mixed with 6% (w/w) dextran having an average molecular weight of 500,000 and 15% (w/w) of polyethyleneglycol having an average molecular weight of 6,000. The mixture was stirred vigorously with a motor driven stirrer until all of the polyethyleneglycol was in solution whereupon it was allowed to stand at room temperature until phase separation was complete. The phase ratio (v/v), top to bottom, was 3.69:1. The phases were separated by removing the top phase from the bottom phase via siphon. The enzymes content of the top phase (PEG) were 66.1% of the original protease and 4.7% of the original amylase. The enzymes content in the bottom phase (dextran) were 95.3% of the original amylase and 33.9% of the original protease.

EXAMPLE III

A filtrate from the fermentation of *B. amyloliquefacieus* was mixed with 15.3% (w/w) of polyethyleneglycol having an average molecular weight of 6,000 and 6% (w/w) of dextran, DEAE-dextran or dextran sulphate, all of which polymers had an average molecular weight of 500,000. Each mixture was stirred until all of the polyethyleneglycol was in solution and processed as previously described. The phase ratio and enzyme distribution in each phase are set out in Table I.

TABLE 1

| Dextran Derivative | $^1V_T/V_B$ | % Enzyme Distribution | | | |
|---|---|---|---|---|---|
| | | Top | | Bottom | |
| | | Amylase | Protease | Amylase | Protease |
| None | 4.1 | 2.6 | 62.1 | 97.6 | 37.9 |
| DEAE | 3.4 | 1.6 | 35.6 | 98.4 | 64.1 |
| Sulphate | 4.1 | 15.3 | 3.8 | 84.7 | 96.2 |

$^1$Polymer phase ratio (top to bottom)

EXAMPLE IV

A study of the effect of polyethyleneglycol (average molecular weight of 6,000) concentration on the enzyme partition coefficient, phase ratio and total enzyme distribution was conducted by varying the amounts of filtrate and polyethyleneglycol addition to the test system. Dextran (average molecular weight 500,000) concentration was kept constant throughout the experiment as 6% (w/w). The results are set out in Table 2.

TABLE 2

Effect of PEG Concentration on Enzyme Distribution and Phase Separation

| % (W/W) | | | $^1K$ | K Pro- | $^5G$ | G |
|---|---|---|---|---|---|---|
| Filtrate | PEG | $V_T/V_B$ | Amylase | tease | Amylase | Protease |
| 90.50 | 3.50 | 0.62 | 0.502 | 1.21 | 0.311 | 0.750 |
| 89.23 | 4.77 | 1.22 | 0.397 | 1.06 | 0.484 | 1.287 |
| 84.35 | 9.65 | 2.78 | 0.104 | 0.85 | 0.289 | 2.361 |
| 81.60 | 12.40 | 3.44 | 0.044 | 0.72 | 0.150 | 2.479 |
| 78.90 | 15.10 | 4.08 | 0.013 | 0.66 | 0.053 | 2.697 |
| 76.40 | 17.60 | 5.14 | 0.006 | 0.63 | 0.032 | 3.249 |

$^1K = \frac{^2C_T}{^3C_B}$, enzyme partition coefficient $^2C_T$ = Concentration of enzyme in the top phase
$^3C_B$ = Concentration of enzyme in the bottom phase $^5G = K \frac{V_T}{V_B}$, ratio of total enzyme distribution It has been observed, as illustrated by the above table, that when the PEG concentration in the mixture is increased, the ratio of the total protease distribution (K VT/VB) increases and the ratio of the total amylase distribution (K VT/VB) decreases. This phenomenon is due mainly to the drastic increase of the VT/VB. The ratio of the total protease distribution increases occur because the protease enzyme partition coefficient (K) decreases so slightly, such that the ratio VT/VB overtakes these values, thus giving rise to increases in the total protease distribution ratio. The opposite aspect happens with the distribution ratio for total amylase because the amylase enzyme partition coefficient (K) decreases so drastically that the ratio of the total amylase distribution cannot equalize the increase of the VT/VB ratio, thus effecting decreases in the total amylase distribution ratios.

EXAMPLE V

To investigate the effect of polyethyleneglycol (PEG-8000, average molecular weight 8000) concentration on the phase ratio, the partition coefficient and the enzyme distribution, various amounts of the filtrate and PEG-8000 were mixed with a constant amount of BETZ-1180 polymer kept constant as 20% (w/w) of the mixture. The results are set out in Table 3.

TABLE 3

The Effect of PEG Concentration on the Phase Ratio, the Partition Coefficient and the ratio of Enzyme Distribution

| % (W/W) | | | Protease (Top) | | Amylase (Bottom) | |
|---|---|---|---|---|---|---|
| Filtrate | PEG | $V_T/V_B$ | K | G | K | G |
| 76 | 4 | 2.21 | 1.64 | 3.62 | 0.79 | 1.72 |
| 72 | 8 | 2.16 | 1.23 | 2.66 | 0.21 | 0.46 |
| 68 | 12 | 2.30 | 1.02 | 2.35 | 0.07 | 0.15 |
| 64 | 16 | 3.00 | 0.92 | 2.75 | 0.03 | 0.08 |
| 60 | 20 | 3.19 | 0.98 | 3.14 | 0.015 | 0.05 |
| 56 | 24 | 2.95 | 1.16 | 3.42 | 0.013 | 0.04 |

The increase in PEG concentration significantly affects the partition coefficient and the ratio of enzyme distribution of the amylase but it is not so in the case of the protease. The phase ratio is moderately affected by the PEG concentration.

EXAMPLE VI

To investigate the effect of BETZ-1180 polymer concentration on the phase ratio, the partition coefficient and the ratio enzyme distribution, various amounts of the filtrate and BETZ-1180 were mixed with a constant amount of PEG-8000 kept as 12% (w/w) of the mixture. The results are set out in Table 4.

TABLE 4

The Effect of Betz-1180 Concentration on the Phase Ratio, the Partition Coefficient and the Ratio of Enzyme Distribution

| % (W/W) | | | Protease (Top) | | Amylase (Bottom) | |
|---|---|---|---|---|---|---|
| Filtrate | Betz-1180 | $V_T/V_B$ | K | G | K | G |
| 84.7 | 3.3 | 20.1 | 0.96 | 19.3 | 0.38 | 7.58 |
| 81.3 | 6.7 | 10.1 | 1.06 | 10.7 | 0.18 | 1.85 |
| 78.0 | 10.0 | 6.0 | 1.00 | 6.0 | 0.12 | 0.73 |
| 74.7 | 13.3 | 4.1 | 0.93 | 3.8 | 0.10 | 0.41 |
| 71.3 | 16.7 | 3.1 | 1.01 | 3.1 | 0.08 | 0.26 |
| 68.0 | 20.0 | 2.6 | 0.95 | 2.5 | 0.07 | 0.19 |

The phase ratio is significantly affected by the addition of the Betz-1180. The partition coefficient of the protease is not affected by the Betz-1180 concentration but the ratio of enzyme distributions are greatly affected because of the change in the phase ratio. In the case of amylase, both K and G values are greatly affected by the Betz-1180 concentration.

What is claimed is:

1. In combination with the method of fermenting an enzyme producing microorganism capable of producing protease and amylase to produce a fermentation broth containing extracellular protease and amylase and filtering this broth to provide a cell-free filtrate containing these enzymes, the improvement which comprises the steps of:
   (a) adding low molecular weight polyethyleneglycol and a high molecular weight cationic polymer selected from the group of epihalohydrin/polyamine copolymers and dextran or a mixture thereof of the filtrate;

(b) providing sufficient agitation to mix the two polymers and the filtrate and allowing phase separation to occur between the polyethyleneglycol containing phase and the epihalohydrin/polyamine copolymer or dextran containing phase to provide a polyethyleneglycol containing phase rich in protease relative to amylase and an epihalohydrin/polyamine copolymer or dextran containing phase rich in amylase relative to protease;

(c) separating the phases formed in step (b);

(d) recovering the enzymes in the polyethyleneglycol containing phase to provide a protease/amylase product rich in protease; and/or (e) recovering the enzymes in the epihalohydrin/polyamine copolymer or dextran containing phase to provide a protease/amylase product which is rich in amylase.

2. The method of claim 1 wherein the enzyme producing microorganism is *Bacillus amyloliquefacieus*.

3. The method of claim 1 wherein the cationic epihalohydrin/polyamine copolymer has a molecular weight of from about 4,000 to 600,000.

4. The molecular weight of claim 3 wherein the molecular weight is from 15,000 to 25,000.

5. The method of claim 1 wherein the polyethyleneglycol has a molecular weight of from 1,000 to 10,000.

6. The method of claim 1 wherein the molecular weight is from 4,000 to 8,000.

7. The method of claim 1 wherein the high molecular weight polymer is dextran having a molecular weight of from about 110,000 to 2,000,000.

8. The method of claim 7 wherein the molecular weight is from about 400,000 to 600,000.

9. The method of claim 1 wherein an epihalohydrin/polyamine copolymer in an amount of from 1.5 to 60 weight percent of the filtrate is added thereto.

10. The method of claim 9 wherein the amount of polyethyleneglycol added is from 0.5 to 30 weight percent of the filtrate.

11. The method of claim 1 wherein dextran in an amount of from 0.5 to 15 weight percent of the filtrate is added thereto.

12. The method of claim 11 wherein the amount of polyethyleneglycol added is from 1.0 to 10 weight percent of the filtrate.

* * * * *